(12) United States Patent
Feierabend et al.

(10) Patent No.: US 7,096,712 B2
(45) Date of Patent: Aug. 29, 2006

(54) MATERIAL TESTING SYSTEM FOR TURBINES

(75) Inventors: Jerry Glynn Feierabend, Katy, TX (US); David J. Blumer, Bartlesville, OK (US); Thomas Austin, Eagle River, AK (US); Sung-I Johnson, Houston, TX (US); Richard D. Sloan, Soldotna, AK (US); Bradley A. Neugebauer, Anchorage, AK (US); Randall Lee Heald, Bartlesville, OK (US); Mark F. Jerling, Waukesha, WI (US); Peter M. Bradshaw, Anchorage, AK (US)

(73) Assignee: ConocoPhillips Company, Houston, TX (US)

( * ) Notice: Subject to any disclaimer, the term of this patent is extended or adjusted under 35 U.S.C. 154(b) by 72 days.

(21) Appl. No.: 10/464,905

(22) Filed: Jun. 18, 2003

(65) Prior Publication Data

US 2004/0206171 A1 Oct. 21, 2004

Related U.S. Application Data

(60) Provisional application No. 60/464,324, filed on Apr. 21, 2003.

(51) Int. Cl.
*G01N 3/56* (2006.01)
*G01N 17/00* (2006.01)
*F04D 29/02* (2006.01)

(52) U.S. Cl. .................. 73/7; 73/86; 73/866; 416/175; 416/223 R; 416/224; 416/241 R

(58) Field of Classification Search .............. 73/7, 73/8, 9, 78, 83, 86, 87, 662, 663, 671, 841, 73/855, 856, 858, 860, 866; 416/223 R, 416/224, 229 R, 241 R, 241 A, 241 B, 175
See application file for complete search history.

(56) References Cited

U.S. PATENT DOCUMENTS

| 1,476,775 | A | * | 12/1923 | Sproull | 73/7 |
| 2,414,439 | A | * | 1/1947 | Brandon | 73/7 |
| 3,229,498 | A | * | 1/1966 | Oakes | 73/7 |
| 3,551,067 | A | * | 12/1970 | Wissman | 415/134 |
| 3,678,559 | A | * | 7/1972 | Zilkalns | 29/281.6 |
| 3,861,825 | A | * | 1/1975 | Blom | 415/199.3 |
| 3,932,941 | A | * | 1/1976 | Ormsby | 73/7 |
| 4,275,966 | A | | 6/1981 | Kleesattel | 356/626 |
| 4,443,152 | A | * | 4/1984 | Wong et al. | 415/143 |
| 4,493,206 | A | * | 1/1985 | Johnson et al. | 73/7 |
| 4,671,740 | A | * | 6/1987 | Ormiston et al. | 416/241 B |
| 5,017,087 | A | * | 5/1991 | Sneddon | 415/72 |
| 5,187,542 | A | * | 2/1993 | Madzsar | 356/300 |
| 5,380,482 | A | | 1/1995 | Maginnis et al. | 419/33 |
| 5,514,329 | A | | 5/1996 | McCaul et al. | 420/56 |

(Continued)

FOREIGN PATENT DOCUMENTS

DE 3816148 A1 * 11/1989

(Continued)

*Primary Examiner*—Hezron Williams
*Assistant Examiner*—David A. Rogers
(74) *Attorney, Agent, or Firm*—Kameron D. Kelly; Ryan N. Cross

(57) ABSTRACT

The wear resistance of impellers used in multi-stage turbine pumps is tested by using a multi-stage turbine pump having impellers with different physical properties to pump a fluid containing small amounts of an abrasive material. After the fluid has been pumped for a time period sufficient to provide measurable wear to the impellers, the impellers are inspected to determine their relative resistance to wear.

10 Claims, 2 Drawing Sheets

U.S. PATENT DOCUMENTS

Figure 1:
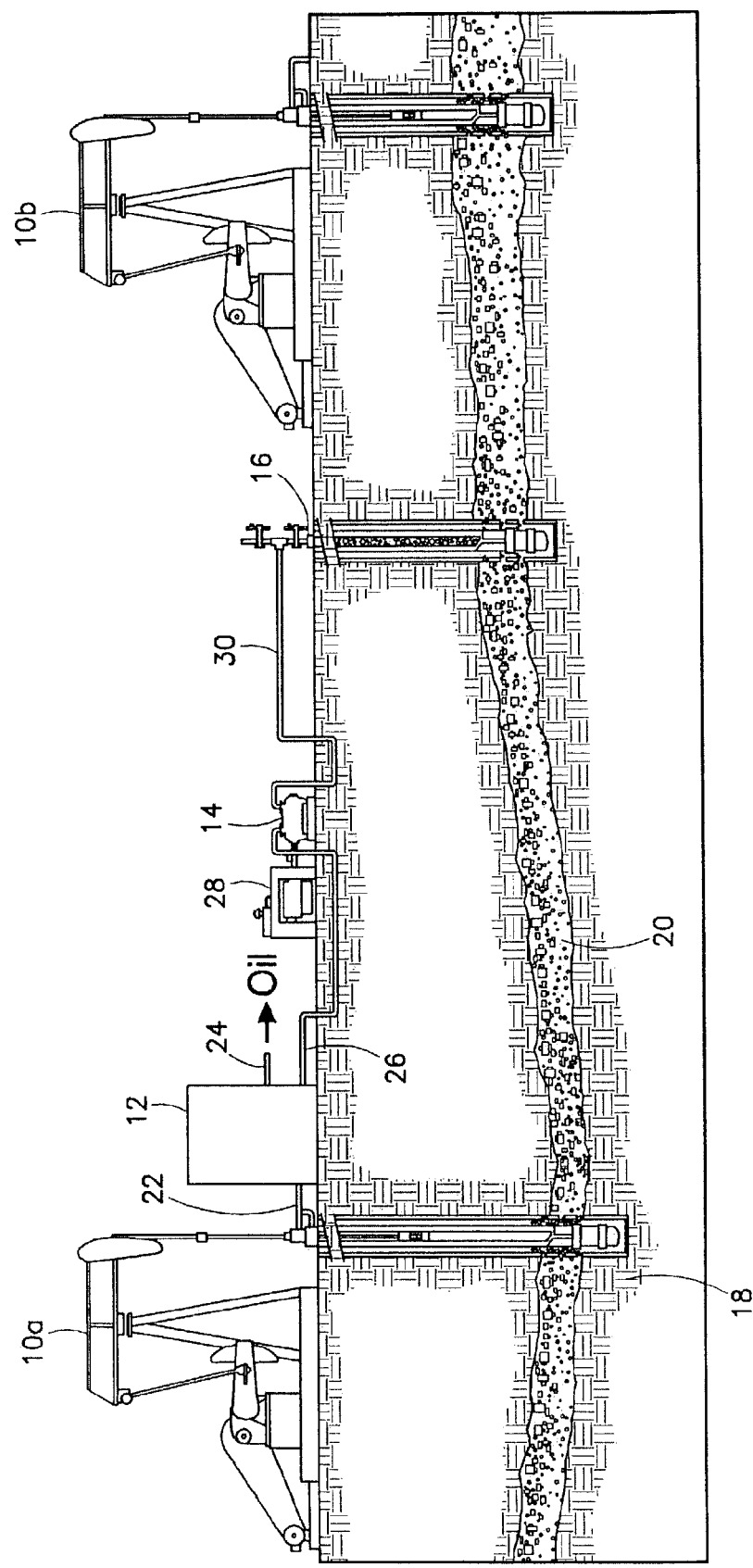

| | | | |
|---|---|---|---|
| 5,547,770 A * | 8/1996 | Meelu et al. | 428/678 |
| 5,599,164 A * | 2/1997 | Murray | 415/144 |
| 5,683,226 A * | 11/1997 | Clark et al. | 415/200 |
| 5,707,740 A * | 1/1998 | Goodwin | 428/410 |
| 6,127,044 A * | 10/2000 | Yamamoto et al. | 428/603 |
| 6,227,796 B1 * | 5/2001 | Markovitch | 415/90 |
| 6,230,544 B1 * | 5/2001 | Matsubara et al. | 73/7 |
| 6,257,217 B1 * | 7/2001 | Yamazaki et al. | 123/668 |
| 6,343,909 B1 * | 2/2002 | Springer et al. | 415/71 |
| 6,510,729 B1 * | 1/2003 | Bonnevie et al. | 73/86 |
| 6,527,512 B1 * | 3/2003 | Bertin et al. | 415/200 |
| 6,626,025 B1 * | 9/2003 | Potyrailo et al. | 73/7 |
| 6,649,682 B1 * | 11/2003 | Breton et al. | 524/404 |
| 6,797,335 B1 * | 9/2004 | Paderov et al. | 427/530 |
| 2002/0083761 A1 * | 7/2002 | Swain et al. | 73/86 |
| 2002/0189722 A1 * | 12/2002 | Hasz et al. | 148/528 |
| 2003/0059542 A1 * | 3/2003 | Creech et al. | 427/385.5 |
| 2003/0110827 A1 * | 6/2003 | Kamitani et al. | 73/7 |
| 2003/0170120 A1 * | 9/2003 | Grunke et al. | 415/174.4 |
| 2003/0183529 A1 * | 10/2003 | Ohara et al. | 205/109 |
| 2004/0022949 A1 * | 2/2004 | Hasezaki et al. | 427/376.2 |

FOREIGN PATENT DOCUMENTS

| | | | |
|---|---|---|---|
| EP | 90980 A | * | 10/1983 |
| EP | 90980 A1 | * | 10/1983 |
| EP | 0939676 | | 3/2002 |
| GB | 1299308 A | * | 12/1972 |
| GB | 2141175 A | * | 12/1984 |
| JP | 59068599 A | * | 4/1984 |

* cited by examiner

MATERIAL TESTING SYSTEM FOR TURBINES

RELATED APPLICATIONS

This application claims the priority benefit under 35 U.S.C. Section 119(e) of U.S. Provisional Patent Application Ser. No. 60/464,324, filed Apr. 21, 2003, the entire disclosure of which is incorporated herein by reference.

BACKGROUND OF THE INVENTION

1. Field of the Invention

The present invention relates generally to multi-stage turbine pumps. In another aspect, the invention concerns a system for testing the wear resistance of impellers used in multi-stage turbine pumps.

2. Description of the Prior Art

Multi-stage turbine pumps are commonly employed in a variety of different applications. In one application, multi-stage turbine pumps are used as injection pumps for oilfield water flood operations. Frequently, the water pumped by the injection pump to the injection well is produced water that has previously been extracted from a subterranean formation along with oil, and subsequently separated from the oil.

One common problem encountered when using a produced water stream for water flood operations is that the produced water stream can contain small quantities of abrasive materials. Typically, the abrasive materials include minute sand particles which were produced along with oil and water from the subterranean formation. Such small sand particles can be difficult and expensive to entirely remove from the produced water stream. Thus, the produced water pumped to injection wells for water flooding operations inevitably contains at least a small amount of sand particles. These sand particles can cause significant wear on the impellers of a multi-stage turbine pump used to pump the produced water to the injection well. Although there has been much speculation as to which materials and/or coatings are best suited for constructing wear-resistant impellers, there has never been an adequate method for comparatively testing which materials or coatings work best in multi-stage turbine pumps used to pump produced water to injection wells.

OBJECTS AND SUMMARY OF THE INVENTION

It is therefore an object of the present invention to provide an impeller testing method which allows for an accurate comparison of the wear resistance of various impeller materials and/or coatings so that an optimum material and/or coating can be determined. It should be understood that the above-listed object is only exemplary. Further, there is no requirement that this object be accomplished by the invention described and claimed herein.

Accordingly, in one embodiment of the present invention, there is provided an impeller testing method comprising the steps of: (a) pumping a fluid containing an abrasive material through a multi-stage pump, with the multi-stage pump including at least two impellers having different physical properties; and (b) subsequent to step (a), comparing the wear of the two impellers to determine whether one of the impellers resists wear better than the other impeller.

In another embodiment of the present invention, there is provided a petroleum production method comprising the steps of: (a) producing a mixture of oil and water from a subterranean formation; (b) separating the mixture of oil and water into an oil-rich stream and a water-rich stream, with the water-rich stream containing small amounts of sand produced from the subterranean formation; (c) using a multi-stage injection pump to inject the water-rich stream into the subterranean formation, with the multi-stage injection pump comprising at least two impellers formed of different materials; and (d) subsequent to step (c), inspecting the wear of the two impellers formed of different materials.

In still another embodiment of the present invention, there is provided a multi-stage turbine pump comprising a casing and a rotor. The casing defines a fluid inlet and a fluid outlet. The rotor is disposed in the casing and is operable to rotate relative to the casing. The rotor includes a plurality of impellers spaced along the axis of rotation of the rotor. At least two of the impellers of the rotor have different physical properties.

In yet another embodiment of the present invention, there is provided a petroleum production system comprising a producing well, a separation facility, a multi-stage injection pump, and an injection well. The producing well is operable to produce a mixture of oil and water from a subterranean formation. The separation facility is fluidly coupled to the producing well and is operable to separate the mixture of oil and water into an oil-rich stream and a water-rich stream. The water-rich stream contains a small amount of sand produced from the subterranean formation. The multi-stage injection pump is fluidly coupled to the separation facility and is operable to pump the water-rich stream. The injection pump comprises a plurality of impellers, with at least two of the impellers being formed of materials having different physical properties. The injection well is fluidly coupled to the multi-stage injection pump and is operable to receive the pumped water-rich stream from the multi-stage injection pump and discharge the pumped water-rich stream into the subterranean formation.

BRIEF DESCRIPTION OF THE DRAWING FIGURES

Figure 2:
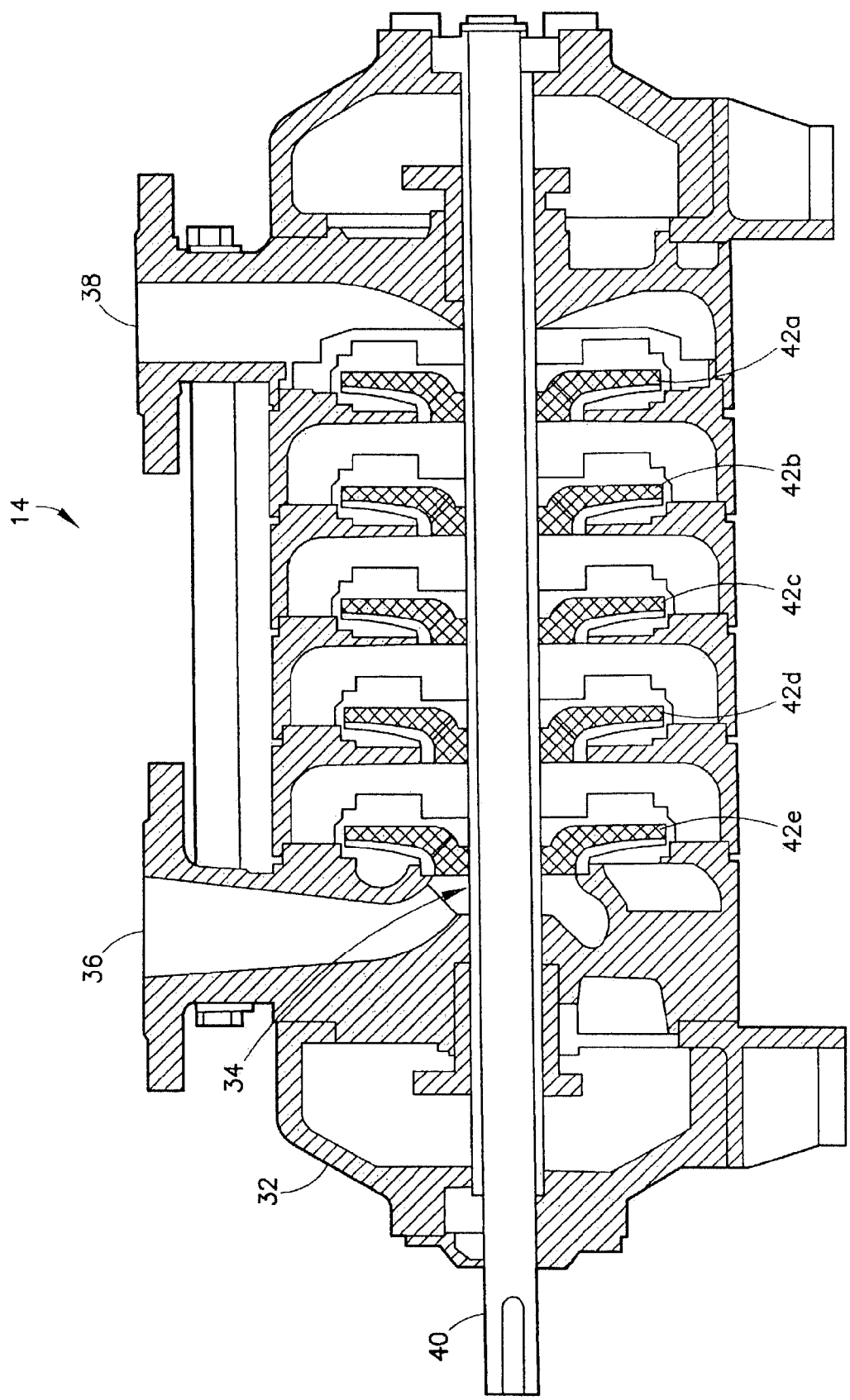

A preferred embodiment of the present invention is described in detail below with reference to the attached drawing figures, wherein:

FIG. 1 is a schematic representation of an oilfield production system which utilizes a multi-stage turbine pump to pump water produced from a subterranean formation back into the subterranean formation for water flooding operations; and FIG. 2 is a sectional view of a multi-stage turbine pump, particularly illustrating a plurality of impellers used in various stages of the pump to force water from an inlet of the pump to an outlet of the pump.

DETAILED DESCRIPTION OF THE PREFERRED EMBODIMENT

Referring initially to FIG. 1, a simplified petroleum production system is illustrated as including producing wells 10a,b an oilfield separation facility 12, an injection pump 14, and an injection well 16. Producing wells 10a,b extend into subterranean formation 18 and produce oil and water from a reservoir 20. The produced oil and water mixture is transported from first producing well 10a to separation facility 12 via conduit 22. In separation facility 12, the produced oil and water mixture is separated into an oil-rich stream which exits separation facility 12 via conduit 24 and a water-rich stream which exits separation facility 12 via conduit 26. Separation facility 12 can also be operable to separate a substantial portion of the sand particles present in the produced oil and water mixture entering separation facility 12 via conduit 22. Although separation facility 12 may remove a significant portion of the sand particles from the produced oil and water mixture, the water-rich stream exiting separation facility 12 via conduit 26 inevitably contains a small amount of minute sand particles.

The water-rich stream exiting separation facility 12 is transported via conduit 26 to multi-stage turbine pump 14. Pump 14 is typically driven by a motor 28 and is operable to increase the pressure of the water-rich stream to a level sufficient for water flooding operations. The pumped water-rich stream from injection pump 14 is then transported to injection well 16 via conduit 30. Injection well 16 extends into subterranean formation 18 and is operable to discharge the water-rich stream into reservoir 20 to thereby help force oil towards producing wells 10a,b.

Referring to FIG. 2, multi-stage turbine pump 14 is illustrated as generally including a casing 32 and a rotor 34. Casing 32 defines a fluid inlet 36 for receiving the water-rich stream from conduit 26 (FIG. 1) and a fluid outlet 38 for discharging the water-rich stream into conduit 30 (FIG. 1). Rotor 34 is coupled to and rotatable relative to casing 32. Rotor 34 generally includes a drive shaft 40 and a plurality of impellers 42a–e spaced along the axis of rotation of drive shaft 40. When rotor 34 is rotated relative to casing 32, impellers 42a–c are operable to force the water-rich stream through casing 32 from inlet 36 to outlet 38.

In a preferred embodiment of the present invention, each of the impellers 42a–e possesses different physical properties which impart unique wear resistance to each impeller 42a–e. These different physical properties can be exhibited due to forming the impellers with different base materials, coating the impellers with different materials, and/or exposing the impellers to different thermal treatment techniques. Various base materials, coatings, and thermal treatments suitable for impellers used in multi-stage turbine pumps are well known in the art.

When multi-stage turbine pump 14 is used to pump the water-rich stream containing small amounts of sand, the abrasiveness of the sand causes portions of the impellers 42a–e to erode. After pump 14 has been used to pump a water-rich stream for a time period sufficient to provide measurable erosion of at least one of the impellers 42a–c, the wear of impellers 42a–e can be observed. Typically, a visual inspection of the amount of wear of impellers 42a–e is adequate to determine the relative abilities of the various impellers 42a–e to resist wear. However, in certain instances, precise measurements of various dimensions of impellers 42a–e may be required to determine and compare the relative wear resistance of impellers 42a–e.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. An impeller testing method comprising the steps of:
   (a) pumping a fluid containing an abrasive material through a multi-stage pump, and using the multi-stage pump to inject the fluid into a subterranean formation, said multi-stage pump including at least two impellers formed of different base materials; and
   (b) subsequent to step (a), comparing the wear of said at least two of the impellers to determine whether one of the impellers resists wear better than another of the impellers.

2. The impeller testing method of claim 1,
   at least a portion of said different base materials being located at the surfaces of said at least two of the impellers.

3. The impeller testing method of claim 2,
   wherein said at least two of the impellers have been subjected to different surface treatments to thereby form said different base materials at the surfaces of said at least two of the impellers.

4. The impeller testing method of claim 1,
   said fluid comprising predominately water.

5. The impeller testing method of claim 4,
   said abrasive material comprising sand.

6. The impeller testing method of claim 1,
   step (b) including visually comparing the wear of said at least two of the impellers.

7. The impeller testing method of claim 1,
   step (b) including measuring the amount of said at least two of the impellers which has worn away during step (a).

8. An impeller testing method comprising the steps of:
   (a) injecting a liquid containing abrasive particles into a subterranean formation using a multi-stage turbine pump, said pump comprising a casing and a rotor rotatably received in the casing, said rotor comprising a drive shaft and at least two impellers coupled to the drive shaft, said impellers being spaced from one another along the axis of rotation of said drive shaft, said impellers being formed of different base materials; and
   (b) subsequent to step (a), visually comparing the impellers to determine whether one of the impellers resists wear better than the other.

9. The impeller testing method of claim 8,
   said liquid comprising predominately water,
   said abrasive particles comprising predominately sand.

10. The impeller testing method of claim 8,
    said different base materials causing different wear resistance properties at the surface of said impellers.

* * * * *